United States Patent [19]

Shanzer et al.

[11] Patent Number: 4,966,997

[45] Date of Patent: Oct. 30, 1990

[54] TRISHYDROXAMIC ACIDS

[75] Inventors: Abraham Shanzer, Rishon Le Zion; Jacqueline Libman; Shneior Lifson, both of Rehovot, all of Israel

[73] Assignee: Yeda Research and Development Co., Ltd., Rehovot, Israel

[21] Appl. No.: 255,584

[22] Filed: Oct. 11, 1988

[51] Int. Cl.$^5$ .............................................. C07C 83/10
[52] U.S. Cl. .................................. 562/623; 210/688; 435/244; 514/575
[58] Field of Search ........................................ 562/623

[56] References Cited

U.S. PATENT DOCUMENTS 3,247,197  4/1966  Gaeumann et al. ................ 562/623

Primary Examiner—J. E. Evans
Attorney, Agent, or Firm—Browdy and Neimark

[57] ABSTRACT

Ligand compounds useful as extractants of certain metals from solutions. Effective also as promoters of the growth of microorganisms.

A process for the preparation of such hexadentate ligands and methods of selective extraction of transition and related metal ions from admixtures with other metals.

11 Claims, No Drawings

TRISHYDROXAMIC ACIDS

FIELD OF THE INVENTION

There are provided compounds which are active agents for use as selective metal extractants and also for further purposes such as promoters of the growth of certain microorganisms. The compounds of the invention are hexadentate ligands and are effective in the separation of various cations, such as trivalent iron from mixtures with bivalent copper; of zinc from mixtures with cadmium, etc. The invention also relates to a process for the production of such compounds.

BACKGROUND OF THE INVENTION

Separation, purification, and analysis of metal ions is of great importance in many diverse areas. Examples are hydrometallurgy and electroplating processes, metal recovery and waste treatment, the preparation of high purity materials for the electronic and laser industry and the analysis of trace metals in body fluids. Two of the methods that are inherently applicable to most of these fields are solvent extraction and membrane technologies. Solvent extraction has extensively been applied for the separation of metal ions in bulk quantities in hydrometallurgic processes. Over the years, much emphasis has been placed on improving the performance of a very small number of simple ligands by carefully modifying extraction conditions such as pH, masking agents, stripping agents and the nature of the organic solvent. On the other hand, only marginal efforts have been devoted to the design of tailor-made ligands that would be inherently fit to extract a specific metal ion in the presence of many others. The subject of the present application involves binders that selectively extract a specific metal ion from a mixture of many. Examples are a hexavalent ligand that separates $Fe^{3+}$ from a mixture of $Fe^{3+}$ and $Cu^{2+}$ and a hexavalent ligand that preferentially extracts $Zn^{2+}$ from a mixture of $Zn^{2+}$ and $Cd^{2+}$. The iron binders among these compounds act as growth promoters of microorganisms by simulating the properties of the natural iron binder ferrichrome.

SUMMARY OF THE INVENTION

There are provided compounds which are active agents for use as selective metal extractants and also for further purposes such as promoters of the growth of certain microorganisms. The compounds of the invention are hexadentate ligands and are effective in the separation of various cations, such as trivalent iron from mixtures with bivalent copper; of zinc from mixtures with cadmium, etc. The invention also relates to a process for the production of such compounds.

The hexadentate ligand compounds of the present invention are designed in a modular manner and fulfil the requirements:

i. they are characterized by a specific ion binding cavity to fit a specific metal ion;

ii. and create a lipophilic envelope.

The cavity is generated by three hydroxamate groups as binding sites. These groups are organized by the molecules' skeleton to form octahedral cavities of appropriate size. The lipophilic envelope is created by the use of lipophilic side chains to attain the solubility of the molecule and of its complex in lipid membranes.

Hydroxamate groups were chosen as ion binding groups in view of three major considerations: (i) their high binding affinity to a large range of metal ions, (ii) their pH dependent binding properties that allow to control metal uptake on one side of the membrane and metal release on the other side, and (iii) their capability to form electrically non-charged complexes thereby enhancing solubility in lipids.

According to this general principle ion binders and carriers were designed and synthesized in a modular fashion. The planned modularity simplifies synthesis on the one hand, and allows variability in the assembly of the molecules on the other. The family of these may be presented by the general formula:

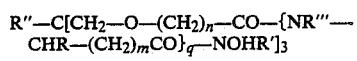

wherein

R, R', R" and R''' are independently selected from —H, alkyl, aryl, aralkyl, —COOR, —CONHR and —CONR$_2$;

n is 1 or 2, m is 0, 1 or 2; q is 0 or 1.

By way of example, the synthesis of compounds of the above formula wherein R' is methyl, R" is ethyl, R is alkyl, and n is 2, m is 0 and q is 1, is illustrated as follows:

(i) Alkylation of the parent alcohol with acrylonitrile, hydrolysis, and subsequent esterification with pentachlorophenol

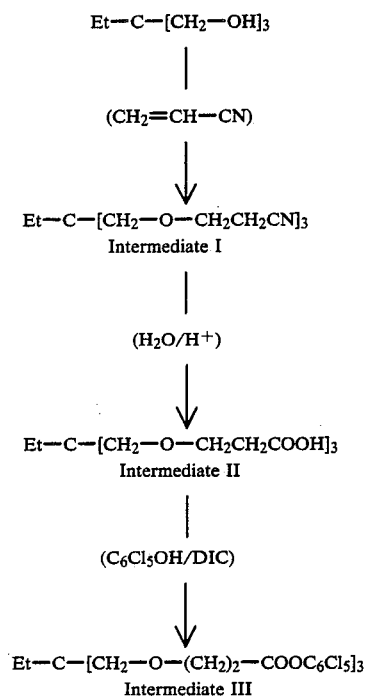

where DIC=Diisopropylcarbodiimide.

(ii) Preparation of the amino-hydroxamate residues by esterification of the chosen protected amino acid with pentachlorophenol, reaction with methyl hydroxylamine and removal of the protecting group by hydrogenation:

CbzNR'''CHRCOOH

↓ (HOC₆Cl₅/DIC)

CbzNR'''CHRCOOC₆Cl₅
Intermediate IV

↓ (CH₃NHOH)

CbzNR'''CHRCONOHCH₃
Intermediate V

↓ (H₂/Pd)

HR''' NCHRCONOHMe
Intermediate VI

Cbz=Carbobenzoxy, and (iii) Condensation of the acid derivative with amino hydroxamate to the desired final products.

EtC[CH₂O(CH₂)₂COOC₆Cl₅]₃

|
+ Intermediate VI
|

EtC[CH₂O(CH₂)₂CONR'''CHRCONOHMe]₃
Product VII

In this manner there were prepared compounds in which R is either iBu, sec. Bu or Me, R'''=H, and a compound where R—R'''=(CH₂)₃, as well as by a similar sequence compounds where n=2, m=1, or 2, q=1, R=H and R'''=H.

EtC[CH₂OCH₂CH₂CONHCRHCONOHCH₃]₃ R = iBU, sec. Bu, Me

EtC[CH₂OCH₂CH₂CON—CONOHCH₃]₃ (with cyclopentyl ring)

EtC[CH₂OCH₂CH₂CONHCH₂CH₂CONOHCH₃]₃

EtC[CH₂OCH₂CH₂CONHCH₂CH₂CH₂CONOHCH₃]₃

In a related sequence of reactions these were prepared compounds where n=1, m=0, 1, 2, q=1, R'=Me, R''=Et and R'''=H. The steps are as follows:

(i) alkylation of the parent alcohol with diazoethylacetate, subsequent hydrolysis and esterification with pentachloropenol:

Et—C—[CH₂—OH]₃

↓ (N₂CHCOOEt/BF₃)

Et—C—[CH₂—O—CH₂—COOEt]₃
Intermediate VIII

↓ (1. H₂O/OH⁻)
  (2. HO—C₆C₅/DIC)

Et—C—[CH₂—O—CH₂—COOC₆Cl₅]₃
Intermediate IX (ii) Preparation of the amino-hydroxamate residues by esterification of the protected amino acid with pentachlorophenol, reaction with methyl hydroxyl amine and removal of the protecting group by hydrogenation.

CbzNR'''CHR(CH₂)ₘCOOH

↓ (HOC₆Cl₅/DIC)

CbzNR'''CHR(CH₂)ₘCOOC₆Cl₅
Intermediate IVa

↓ (CH₃NHOH)

CbzNR'''CHR(CH₂)ₘCONOCH₃
Intermediate Va

↓ (H₂/Pd)

HR'''NCHR(CH₂)ₘCONOHMe
Intermediate VIa

Cbz-Carbobenzoxy and (iii) condensation of the acid derivative with the amino hydroxamate to the desired final products.

EtC[CH$_2$OCH$_2$COOC$_6$Cl$_5$]$_3$
Intermediate IX

|

+ Intermediate VIa

↓

EtC[CH$_2$OCH$_2$CONHCHR(CH$_2$)$_m$CONOHMe]$_3$
Product X

In this manner there were prepared compounds where R=iBu, and m=0, as well as compounds where R=H, and m=1 or 2.

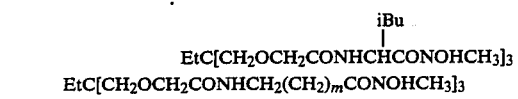

EtC[CH$_2$OCH$_2$CONHCH$_2$(CH$_2$)$_m$CONOHCH$_3$]$_3$ m=1,2.

1. Synthesis of Trishydroxamate VII (n=2, m=0, q=1, R=iBu, R'=Me, R"=Et, R'"=H)

Preparation of Tricarboxylate III 13.4 g triol (0.1 mol) are treated dropwise with 1.0 ml 40% aq. NaOH and then 22 ml (0.33 mol) acrylonitrile (freshly purified by passing through neutral alumina) are added such that the temperature does not exceed 30° C. Then the mixture is stirred overnight at room temperature, neutralized with diluted aq. Hcl, dissolved in 500 ml ethyl acetate, washed with water, dried and concentrated to give 25.45 g trinitrile. The crude product is hydrolyzed by treating 2.93 g with 3.6 ml conc. HCl in an oil bath of 95°-100° C. for 4 hrs. After cooling to room temperature the residue is suspended in ethylacetate, washed with water, dried and concentrated to give 2.49 triacid. 4.9 g of crude triacid are dissolved in 500 ml acetonitrile (dried over alumina), 13.2 g pentachlorophenol and 610 mg dimethylaminopyridine are added, the mixture cooled in an ice bath and treated with 7.5 ml diisopropylcarbodiimide. Then the mixture is allowed to warm up to room temperature and stirred for 1-2 days. Concentration in vacuo and chromatography on silica gel (CCl4-EtOAc 98-2, 95-5) yields 2.5 g of the triscarboxylate III (mp 146°-150° C.).

Preparation of Hydroxamate VI (R=iBu, R'"=H)

5.3 g (0.02 mol) CB$_z$-L-leucine are dissolved in 150 ml acetonitrile (dried over basic alumina), 5.8 g (0.022 mol) pentachlorophenol are added and under cooling 3.9 ml (0.025 mol) diisopropylcarbodiimide. The mixture is stirred for 1 day at room temperature, concentrated, chromatographed on silica gel and then filtered through neutral alumina to provide 10.41 g pure pentachlorophenolate (mp 125°-126° C.). 5.2 g (0.01 mol) of phenolate are dissolved in 50 ml dry methylenechloride and treated with a solution containing 1.04 g (0.0125 mol) methylhydroxyl amine hydrochloride, 1.21 g (0.0125 mol) triethyl amine and 50 mg N-hydroxysuccinimide in 100 ml methylenechloride. The mixture is stirred overnight, concentrated in vacuo and the residue chromatographed on silica gel (chloroform-methanol 99-1) to provide 1.3 g pure CB$_z$-leuhydroxamate (mp 71°-73° C.). 960 mg (0.003 mol) of the latter are dissolved in 100 ml ethanol and hydrogenated at atmospheric pressure in the presence of 500 mg Pd/C, 10%. Filtration, concentration, and chromatography on silica gel (chloroform-methanol 8-2), yields 472 mg of pure hydroxamate VI.

Preparation of Hydroxamate VII (R=iBu, R'"=H)

1.008 g (0.001 mol) triscarboxylate III are dissolved in 50 ml dry methylene chloride and treated with a solution containing 690 mg hydroxamate II, 50 mg N-hydroxysuccinimide and 200 mg imidazole in 50 ml methylenechloride for 2 days. Chromatography of the crude reaction product on silica gel (chloroform, chloroform methanol 95-5 as eluents) yields 255 mg of the trishydroxamate VII (mp 77°-80° C.).

| | | | UV | CD | |
|---|---|---|---|---|---|
| R | R'" | Mp °C. | $\lambda_{max}\epsilon$ (nm) | $\lambda_{ext}$ (nm) | $\Delta\epsilon$ |
| q = 1 | | | | | |
| L-iBu | H | 77-80° C. | 424 2500 | 365,413,450 | −6.8,0.0,+3.4 |
| L-CH$_2$)$_3$ | | 34-38° C. | 428 2550 | 378,430,465 | −4.3,0.0,+1.27 |
| H | Me | oil | 430 1920 | | |
| D-Me | H | oil | 430 2430 | 370,420,455 | +5.2,0.0,−2.0 |
| L-Me | H | oil | 422 2380 | 370,420,455 | −5.2,0.0,+2.0 |
| q = 0 | | | | | |
| — | — | oil | 320 2530 | | |

Physical characteristics of carriers (n = 2, m = 0, R' = Me, R" = Et) and of UV- and CD-data of their ferric ion complexes D- and L- designate the absolute configurations of the amino acids used.

Uses of Ion binders and carriers

Selective metal extraction and transport

Several of the ion binders, when incorporated into bulk membranes, proved to selectively extract and transport a specific metal ion from a mixture of many. Examples are (i) separation of Fe$^{3+}$ from a mixture of Fe$^{3+}$ and Cu$^{2+}$, and (ii) separation of Zn$^{2+}$ from a mixture of Zn$^{2+}$ and Cd$^{2+}$.

For example, quantitative extraction of Fe$^{3+}$ from an equimolar, aq. mixture of Fe$^{3+}$ and Cu$^{2+}$ (3 mM each) was achieved with a 3 mM solution of carrier (n=2, q=0, R'=Me, R"=Et) in chloroform using a U-tube experiment. A chloroformic solution of the same carrier (0.3 mM) when used as "bulk membrane" transported 58% of Fe$^{3+}$ without any traces of contaminating Cu$^{2+}$ from an aqueous source solution containing equimolar amounts (0.3 mM) of Fe$^{3+}$ and Cu$^{2+}$ into a receiver of aqueous 3.0 mM DTPA.

Another carrier (n=2, m=0, q=1, R=iBu, R'=Me, R"=Et, R'"=H) was found to selectively transport Zn$^{2+}$ from a mixture of Zn$^{2+}$ and Cd$^{2+}$ when incorporated into chloroform as bulk membrane.

Growth promotion

Carriers where n=2, m=0, q=0 or 1, R'=CH₃, R''=Et, R=H, alkyl, R'''=H, alkyl, where found to simulate the growth promotion activity of natural ferrichrome towards microorganisms. Specifically, addition of picomolar quantities of these carriers to cultures of *Arthrobacter flavescens* accelerated their growth with an efficiency reaching, and (with R=L-CH₃) even matching that of genuine ferrichrome.

We claims:

1. A compound of the general formula

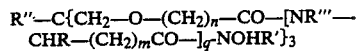

R''—C{CH₂—O—(CH₂)$_n$—CO—[NR'''—CHR—(CH₂)$_m$CO—]$_q$-NOHR'}₃ where R, R', R" and R'" are independently selected from the group consisting of hydrogen, alkyl, aralkyl, aryl, alkyl —COOR, alkyl —CONHR and alkyl —CONR₂, and where n is 1 or 2, m is 0, 1, or 2, q is 0 or 1.

2. A compound according to claim 1, where R' is methyl, R" is ethyl, n is 2, q is 0.

3. A compound of claim 1, wherein R is iso-butyl, R' is methyl, R" is ethyl, R'" is —H, and wherein n=2, m=0 and q=1.

4. A compound according to claim 1, wherein R is —H, or alkyl, R' is methyl, R" is ethyl, R'" is —H or alkyl, n is 2, m is 0 and q is 1.

5. A compound of claim 1, wherein R=R'"=L(CH₂)₃, R' is methyl, R" is ethyl, n is 2, m is 0, q is 1.

6. A compound of claim 1, wherein R=H, R' is methyl, R" is ethyl, R'"=CH₃, n is 2, m is 0, q is 1.

7. A compound of claim 1, wherein R=D—CH₃, R' is methyl, R" is ethyl, R'" is —H, n is 2, m is 0, q is 1.

8. A compound of claim 1, wherein R=L—CH₃, R' is methyl, R" is ethyl, R'"=H, n is 2, m is 0, q is 1.

9. A compound according to claim 1, where R' is methyl, R" is ethyl, n is 1 q is 1.

10. A compound according to claim 1, where R' is methyl, R" is ethyl, R is isobutyl, n is 1, q is 1.

11. A compound according to claim 1 where R' is methyl, R" is ethyl, R is H, n is 1, q is 1, m=1 or 2.